(12) United States Patent
Thakur et al.

(10) Patent No.: US 10,827,932 B2
(45) Date of Patent: Nov. 10, 2020

(54) PREDICTIONS OF WORSENING HEART FAILURE

(71) Applicant: Cardiac Pacemakers, Inc., St. Paul, MN (US)

(72) Inventors: Pramodsingh Hirasingh Thakur, Woodbury, MN (US); Viktoria A. Averina, Shoreview, MN (US); Qi An, Blaine, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 210 days.

(21) Appl. No.: 15/281,992

(22) Filed: Sep. 30, 2016

(65) Prior Publication Data

US 2017/0095160 A1    Apr. 6, 2017

Related U.S. Application Data

(60) Provisional application No. 62/236,416, filed on Oct. 2, 2015.

(51) Int. Cl.
*A61B 5/0205*    (2006.01)
*A61B 5/00*    (2006.01)
(Continued)

(52) U.S. Cl.
CPC .......... *A61B 5/0205* (2013.01); *A61B 5/0538* (2013.01); *A61B 5/7275* (2013.01);
(Continued)

(58) Field of Classification Search
None
See application file for complete search history.

(56) References Cited

U.S. PATENT DOCUMENTS 7,801,591 B1    9/2010    Shusterman
8,116,841 B2    2/2012    Bly et al.
(Continued)

FOREIGN PATENT DOCUMENTS

CN    108290044 A    7/2018
WO    WO-2017059202 A1    4/2017

OTHER PUBLICATIONS

"International Application U.S. Appl. No. PCT/US2016/054682, International Preliminary Report on Patentability dated Apr. 12, 2018", 8 pgs.
(Continued)

*Primary Examiner* — Meredith Weare
(74) *Attorney, Agent, or Firm* — Schwegman Lundberg & Woessner, P.A.

(57) ABSTRACT

Systems and methods for detecting cardiac conditions such as events indicative of worsening heart failure are described. A system can include a sensor circuit to sense a physiological signal, transform one or more first signal portions of the physiological signal into one or more baseline values, and transform one or more second signal portions of the physiological signal into short-term values associated with respective timing information. The system can generate a cardiac condition indicator using a weighted combination of relative difference between the one or more short-term values and the one or more baseline values. The weighting can include one or more weight factors determined according to the timings of the one or more second signal portions. The system can output an indication of a progression over time of the cardiac condition indicator, or deliver therapy according to the cardiac condition indicator.

20 Claims, 9 Drawing Sheets

(51) Int. Cl.
*G16H 40/63* (2018.01)
*A61N 1/365* (2006.01)
*A61B 5/053* (2006.01)
*G16H 50/20* (2018.01)
*A61N 1/362* (2006.01)
*G16H 50/30* (2018.01)
*A61B 5/042* (2006.01)
*A61B 5/021* (2006.01)
*A61B 5/08* (2006.01)
*A61B 5/11* (2006.01)
*A61B 7/02* (2006.01)

(52) U.S. Cl.
CPC .......... *A61N 1/365* (2013.01); *A61N 1/3627* (2013.01); *A61N 1/36521* (2013.01); *G16H 40/63* (2018.01); *G16H 50/20* (2018.01); *G16H 50/30* (2018.01); *A61B 5/021* (2013.01); *A61B 5/0422* (2013.01); *A61B 5/053* (2013.01); *A61B 5/0535* (2013.01); *A61B 5/0816* (2013.01); *A61B 5/1118* (2013.01); *A61B 5/7282* (2013.01); *A61B 7/02* (2013.01)

(56) References Cited

U.S. PATENT DOCUMENTS

| | | |
|---|---|---|
| 8,249,686 B2 | 8/2012 | Libbus et al. |
| 8,285,356 B2 | 10/2012 | Bly et al. |
| 8,374,688 B2 | 2/2013 | Libbus et al. |
| 8,406,868 B2 | 3/2013 | Buschman et al. |
| 8,412,317 B2 | 4/2013 | Mazur |
| 8,423,134 B2 | 4/2013 | Buschman et al. |
| 8,460,189 B2 | 6/2013 | Libbus et al. |
| 8,509,902 B2 | 8/2013 | Cho et al. |
| 8,591,430 B2 | 11/2013 | Amurthur et al. |
| 8,620,425 B2 | 12/2013 | Zhou et al. |
| 8,639,327 B2 | 1/2014 | Zhou et al. |
| 8,684,925 B2 | 4/2014 | Manicka et al. |
| 8,700,143 B2 | 4/2014 | Stylos |
| 8,706,219 B2 | 4/2014 | Feldman et al. |
| 8,706,223 B2 | 4/2014 | Zhou et al. |
| 8,718,752 B2 | 5/2014 | Libbus et al. |
| 8,718,763 B2 | 5/2014 | Zhou et al. |
| 8,725,259 B2 | 5/2014 | Kornet et al. |
| 8,781,582 B2 | 7/2014 | Ziegler et al. |
| 8,781,583 B2 | 7/2014 | Cornelussen et al. |
| 8,790,257 B2 | 7/2014 | Libbus et al. |
| 8,790,259 B2 | 7/2014 | Katra et al. |
| 8,888,699 B2 | 11/2014 | Buschman et al. |
| 8,897,868 B2 | 11/2014 | Mazar et al. |
| 8,965,498 B2 | 2/2015 | Katra et al. |
| 9,125,566 B2 | 9/2015 | Libbus et al. |
| 9,155,893 B2 | 10/2015 | Zhou et al. |
| 9,167,980 B2 | 10/2015 | Ben-David et al. |
| 9,173,615 B2 | 11/2015 | Katra et al. |
| 9,186,089 B2 | 11/2015 | Mazar et al. |
| 9,211,073 B2 | 12/2015 | Banet et al. |
| 9,211,413 B2 | 12/2015 | Ziegler et al. |
| 9,254,094 B2 | 2/2016 | Ben-David et al. |
| 9,259,183 B2 | 2/2016 | Banet et al. |
| 9,320,443 B2 | 4/2016 | Libbus et al. |
| 9,332,941 B2 | 5/2016 | Banet et al. |
| 9,411,936 B2 | 8/2016 | Landrum et al. |
| 9,451,897 B2 | 9/2016 | Mazur et al. |
| 2005/0124900 A1* | 6/2005 | Stadler ................ A61B 5/0031 600/509 |
| 2008/0027349 A1* | 1/2008 | Stylos ................. A61B 5/0537 600/547 |
| 2010/0030292 A1* | 2/2010 | Sarkar .................. A61B 5/053 607/6 |
| 2010/0113888 A1* | 5/2010 | Cho .................... A61B 5/0215 600/301 |
| 2010/0217738 A1* | 8/2010 | Sarel ....................... A61B 5/02 706/47 |
| 2011/0098771 A1* | 4/2011 | Thakur ................ A61B 5/053 607/27 |
| 2012/0089040 A1* | 4/2012 | Stahmann ........... A61B 5/0031 600/528 |
| 2012/0203092 A1 | 8/2012 | Sweeney et al. |
| 2015/0157221 A1 | 6/2015 | An et al. |

OTHER PUBLICATIONS

"International Application Serial No. PCT/US2016/054682, International Search Report dated Dec. 21, 2016", 3 pgs.

"International Application Serial No. PCT/US2016/054682, Written Opinion dated Dec. 21, 2016", 6 pgs.

"European Application Serial No. 16779311.6, Response filed Nov. 30, 2019 to Communication Pursuant to Rules 161(1) and 162 EPC dated May 23, 2018", 12 pgs.

"European Application U.S. Serial No. 16779311.6, Communication Pursuant to Article 94(3) EPC Dec. 10, 2019", 4 pgs.

\* cited by examiner

PREDICTIONS OF WORSENING HEART FAILURE

CLAIM OF PRIORITY

This application claims the benefit of priority under 35 U.S.C. § 119(e) of U.S. Provisional Patent Application Ser. No. 62/236,416, filed on Oct. 2, 2015, which is herein incorporated by reference in its entirety.

TECHNICAL FIELD

This document relates generally to medical devices, and more particularly, to systems, devices and methods for detecting and monitoring events indicative of worsening of congestive heart failure.

BACKGROUND

Congestive heart failure (CHF or HF) is a major health problem and affects many people in the United States alone. CHF patients can have enlarged heart with weakened cardiac muscles, resulting in poor cardiac output of blood. Although CHF is usually a chronic condition, it can occur suddenly. It can affect the left heart, right heart or both sides of the heart. If CHF affects the left ventricle, signals that control the left ventricular contraction are delayed, and the left and tight ventricles do not contract simultaneously. Non-simultaneous contractions of the left and right ventricles further decrease the pumping efficiency of the heart.

In many CHF patients, elevated pulmonary vascular pressures can cause fluid accumulation in the lungs over time. The fluid accumulation can precede or coincide with worsening of HF such as episodes of HF decompensation. The HF decompensation can be characterized by pulmonary or peripheral edema, reduced cardiac output, and symptoms such as fatigue, shortness of breath, and the like.

OVERVIEW

Frequent monitoring of CHF patients and timely detection of thoracic fluid accumulation or other events indicative of HF decompensation status can help prevent worsening of HF in CHF patients, hence reducing cost associated with HF hospitalization. Additionally, identification of patient at an elevated risk of developing future events of worsening HF can help ensure timely treatment, thereby improving the prognosis and patient outcome. Identifying and safely managing the patients having risk of future HF events can avoid unnecessary medical intervention and reduce healthcare cost.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory medical devices can include physiologic sensors which can be configured to sense electrical activity and mechanical function of the heart. The ambulatory medical devices can deliver therapy such as electrical stimulations to target tissues or organs, such as to restore or improve the cardiac function. Some of these devices can provide diagnostic features, such as using transthoracic impedance or other sensor signals to detect a disease or a disease condition. For example, fluid accumulation in the lungs decreases the transthoracic impedance due to the lower resistivity of the fluid than air in the lungs. Fluid accumulation in the lungs can also irritate the pulmonary system and leads to decrease in tidal volume and increase in respiratory rate.

Prediction of a future HF decompensation event, such as by detecting a precipitating event such as increased thoracic fluid accumulation, can be based on a detected change of a sensor signal (such as a thoracic impedance signal) from a reference signal. Desirable performance of a HF decompensation predictor can include one or more of a high sensitivity, a high specificity, or a high positive predictive value (PPV). The sensitivity can be represented as a percentage of actual HF decompensation episodes that are correctly recognized by a detection method. The specificity can be represented as a percentage of actual non-HF decompensation episodes that are correctly recognized as non-HF decompensation events by the detection method. The PPV can be represented as a percentage of the detected HF decompensation episodes, as declared by the detection method, which are actual HF decompensation events. A high sensitivity can help ensure timely intervention to a patient with an impending HF decompensation episode, whereas a high specificity and a high PPV can help avoid unnecessary intervention and added healthcare cost due to false alarms.

HF decompensation detection may be affected by a number of factors including the choice of physiologic sensors or physiological signals. For example, a detector using a physiologic sensor may provide desirable accuracy in HF decompensation event detection in one patient but less sensitive or less specific in another patient. Additionally, the performance of a detector using a particular sensor signal may change over time such as due to patient's disease progression, development of a new medical condition, or other confounding factors attributed to patient's physiologic responses or environmental noise. Techniques such as signal filtering or smoothing can be used to produce a less noisy reference sensor signal, such that a change of the sensor signal from the reference signal can be more reliably predictive of future HF decompensation events. However, signal filtering or smoothing may not be effective in some circumstances and may not yield reliable and accurate detection of HF decompensation, such as when the confounding events or the noise interferences cause long and sustained changes of sensor signal in a direction (which is also known as signal drift over time). On the other hand, a HF decompensation episode may also be preceded by localized, quick, and sharp changes in one or more sensor signals. Such characteristic signal morphologies, if not properly preserved, may deteriorate the performance of the HF decompensation detector, such as leading to a lower sensitivity to detecting a HF decompensation event. At least with these issues in consideration, the present inventors have recognized that there remains a considerable need for improving HF decompensation event detection in CHF patients.

This document discusses, among other things, systems and methods for detecting cardiac conditions such as events indicative of worsening HF. A system can include a sensor circuit to sense a physiological signal, transform one or more first signal portions of the physiological signal into respective one or more baseline values, and transform one or more second signal portions of the physiological signal into respective short-term values associated with respective timing information. The system can generate a cardiac condition indicator using a weighted combination of relative difference between the one or more short-term values and corresponding one or more baseline values. The weighting can include weight factors determined according to the timings of the one or more second signal portions. The system can output an indication of a progression over time of the cardiac condition indicator, or deliver therapy according to the cardiac condition indicator.

In Example 1, a system can comprise a signal input circuit that can receive at least one physiological signal sensed from a patient, a memory circuit, a baseline value generator circuit, a short-term value generator circuit, a comparator circuit, and a cardiac condition detector circuit. The baseline value generator circuit can be coupled to the signal input circuit and the memory circuit. The baseline value generator circuit can generate one or more baseline values using one or more first signal portions of the received at least one physiological signal during one or more first time durations, and to store the one or more baseline values in the memory circuit. The short-term value generator circuit can be coupled to the signal input circuit and the memory circuit. The short-term value generator circuit can generate one or more short-term values using one or more second signal portions of the received at least one physiological signal during one or more second time durations, and to store the one or more short-term values in the memory circuit. The one or more short-term values can be associated with respective timings. The comparator circuit can be coupled to the memory circuit or coupled to both the baseline value generator circuit and the short-term value generator circuit. The comparator circuit can determine a difference between the one or more short-term values and the one or more baseline values. The cardiac condition detector circuit can be coupled to the comparator circuit to determine a cardiac condition indicator using a weighted combination of the difference between the one or more short-term values and the one or more baseline values. The weighting includes one or more weight factors determined according to timings of the one or more first signal portions or the one or more second signal portions.

Example 2 can include, or can optionally be combined with the subject matter of Example 1 to optionally include, an output circuit coupled to the cardiac condition detector circuit, the output circuit configured to generate a human-perceptible presentation of the cardiac condition indicator.

Example 3 can include, or can optionally be combined with the subject matter of one or any combination of Examples 1 or 2 to include, the cardiac condition detector circuit that can determine the cardiac condition indicator using a linear combination of the difference between the one or more short-term values and the one or more baseline values, the difference scaled by a respective weight factor.

Example 4 can include, or can optionally be combined with the subject matter of one or any combination of Examples 1 through 3 to include, the one or more weight factors that are determined as a decay function of time intervals between the timings of the one or more second signal portions and a reference time.

Example 5 can include, or can optionally be combined with the subject matter of Example 4 to optionally include, the decay function that can include at least one of an exponential decay function, a logistic decay function, a logarithm decay function, a linear decay function, or a piece-wise linear decay function.

Example 6 can include, or can optionally be combined with the subject matter of one or any combination of Examples 1 through 5 to include, the short-term value generator circuit that can generate the one or more short-term values using the one or more second signal portions that precede a reference time.

Example 7 can include, or can optionally be combined with the subject matter of one or any combination of Examples 1 through 6 to include, the baseline value generator circuit that can generate the one or more baseline values using a statistical measure of the one or more first signal portions of the received at least one physiological signal.

Example 8 can include, or can optionally be combined with the subject matter of one or any combination of Examples 1 through 7 to include, the short-term value generator circuit that can generate the one or more short-term values using a statistical measure of the one or more second signal portions of the received at least one physiological signal.

Example 9 can include, or can optionally be combined with the subject matter of one or any combination of Examples 1 through 8 to include, a selector circuit coupled to the comparator circuit. The selector circuit can select a subset of the one or more short-term values using the difference between the one or more short-term values and the one or more baseline values. The cardiac condition detector circuit can only use the selected subset of the one or more short-term values to determine the cardiac condition indicator.

Example 10 can include, or can optionally be combined with the subject matter of one or any combination of Examples 1 through 9 to include, the at least one physiological signal that corresponds to an impedance signal, a thoracic impedance signal, a heart sound signal, an activity signal, a respiration signal, or a pressure signal.

Example 11 can include, or can optionally be combined with the subject matter of one or any combination of Examples 1 through 10 to include, the at least one physiological signal that corresponds to intensity of an S3 heart sound.

Example 12 can include, or can optionally be combined with the subject matter of one or any combination of Examples 1 through 11 to include, the baseline value generator circuit that can generate an initial baseline value, and can generate, for each of the one or more short-term values, a corresponding baseline value by updating the initial baseline value using a third portion of the received at least one physiologic signal.

Example 13 can include, or can optionally be combined with the subject matter of one or any combination of Examples 1 through 12 to include, the cardiac condition detector circuit that can determine a progression over time of the cardiac condition indicator, a likelihood of a future heart failure decompensation event, or a heart failure status indicator.

Example 14 can include, or can optionally be combined with the subject matter of one or any combination of Examples 1 through 13 to include, a physiologic sensor that can sense the physiological signal from the patient.

Example 15 can include, or can optionally be combined with the subject matter of one or any combination of Examples 1 through 14 to include, a therapy circuit configured to deliver a therapy to the patient in response to the cardiac condition indicator.

In Example 16, a method can comprise steps of: sensing at least one physiological signal from a patient using a physiologic sensor; generating one or more baseline values using one or more first signal portions of the sensed at least one physiological signal during one or more first time durations; generating one or more short-term values using one or more second signal portions of the sensed at least one physiological signal during one or more second time durations; computing a difference between the one or more short-term values and the one or more baseline values;

determining a cardiac condition indicator using a weighted combination of the difference between the one or more short-term values and the one or more baseline values, wherein the weighting includes one or more weight factors determined according to timings of the one or more first signal portions or the one or more second signal portions.

Example 17 can include, or can optionally be combined with the subject matter of Example 16 to optionally include, generating a human-perceptible presentation of the cardiac condition indicator.

Example 18 can include, or can optionally be combined with the subject matter of Example 16 to optionally include, determining the cardiac condition indicator using a linear combination of the difference between the one or more short-term values and the one or more baseline values, the difference scaled by a respective weight factor.

Example 19 can include, or can optionally be combined with the subject matter of Example 16 to optionally include, determining the one or more weight factors as a decay function of time intervals between the timings of the one or more second signal portions and a reference time. The decay function can include at least one of an exponential decay function, a logistic decay function, a logarithm decay function, a linear decay function, or a piece-wise linear decay function.

Example 20 can include, or can optionally be combined with the subject matter of Example 16 to optionally include, a step of selecting a subset of the one or more short-term values using the difference between the one or more short-term values and the one or more baseline values. The cardiac condition indicator can be determined using only the selected subset of the one or more short-term values to determine the cardiac condition indicator.

Example 21 can include, or can optionally be combined with the subject matter of Example 16 to optionally include, sensing the at least one physiological signal that corresponds to an impedance signal, a thoracic impedance signal, a heart sound signal, an activity signal, a respiration signal, or a pressure signal.

Example 22 can include, or can optionally be combined with the subject matter of Example 16 to optionally include, using the cardiac condition indicator to determine a progression over time of the cardiac condition indicator, a likelihood of a future heart failure decompensation event, or a heart failure status indicator Example 23 can include, or can optionally be combined with the subject matter of Example 16 to optionally include, delivering a therapy to the patient using a therapy circuit in response to the cardiac condition indicator.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting one or more target physiologic events or conditions. The events can include early precursors of a HF decompensation episode. That is, these events can occur well before the systematic manifestation of worsening of HF. Therefore, by detecting the precursor events, the present subject matter can provide a method and device for detecting an impending HF decompensation episode. The systems, devices, and methods described herein may be used to determine cardiac condition such as HF status and/or track progression of the cardiac condition such as worsening of or recovery from a HF event. This system can also be used in the context of other diseases associated with accumulation of thoracic fluid, such as pneumonia.

Figure 1:
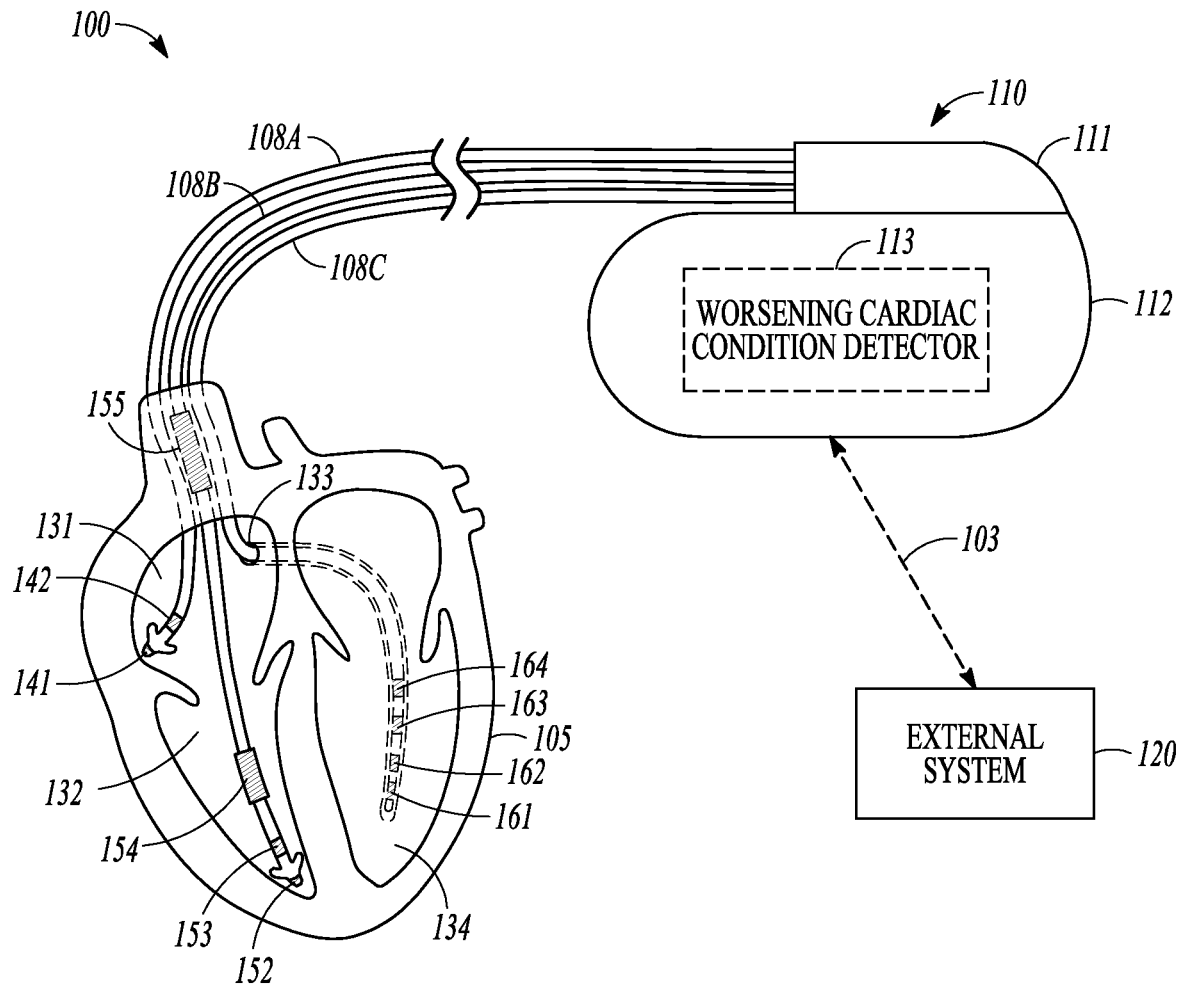
FIG. 1 illustrates generally an example of a cardiac rhythm management (CRM) system and portions of the environment in which the CRM system operates.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can housing 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 can sense impedance such as between electrodes located on one or more of the leads 108A-C or the can housing 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiological signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are contemplated.

As illustrated, the CRM system 100 can include a worsening cardiac condition detector 113. The worsening cardiac condition detector 113 can be configured to receive a physiological signal, such as sensed from the patient using the electrodes on one or more of the leads 108A-C or the can housing 112, or other physiologic sensors deployed on or within the patient and communicated with the IMD 110. Examples of the physiological signals can include impedance signal, thoracic impedance signal, heart sounds signal, pressure signals, respiration signal, and activity signal, among others. The worsening cardiac condition detector 113 can determine a baseline level of the physiological signal, and calculate periodically or continuously accumulated deviations from the baseline level of the physiological signal over a specified period of time. Using accumulated deviations, the worsening cardiac condition detector 113 can detect an event such as a worsening HF event from the patient. The worsening HF event can include one or more early precursors of a HF decompensation episode, or an event indicative of HF progression such as deterioration of HF status. The worsening cardiac condition detector 113 can also be modified to detect recovery of HF status, or other physiologic events such as pulmonary edema, pneumonia, or myocardial infarction, among others. Examples of the worsening cardiac condition detector 113 are described below, such as with reference to FIGS. 2-3.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The worsening cardiac condition detector 113 may be implemented in the external system 120. The external system 120 can be configured to perform HF decompensation event detection such as using data extracted from the IMD 110 or data stored in a memory within the external system 120. Portions of the worsening cardiac condition detector 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
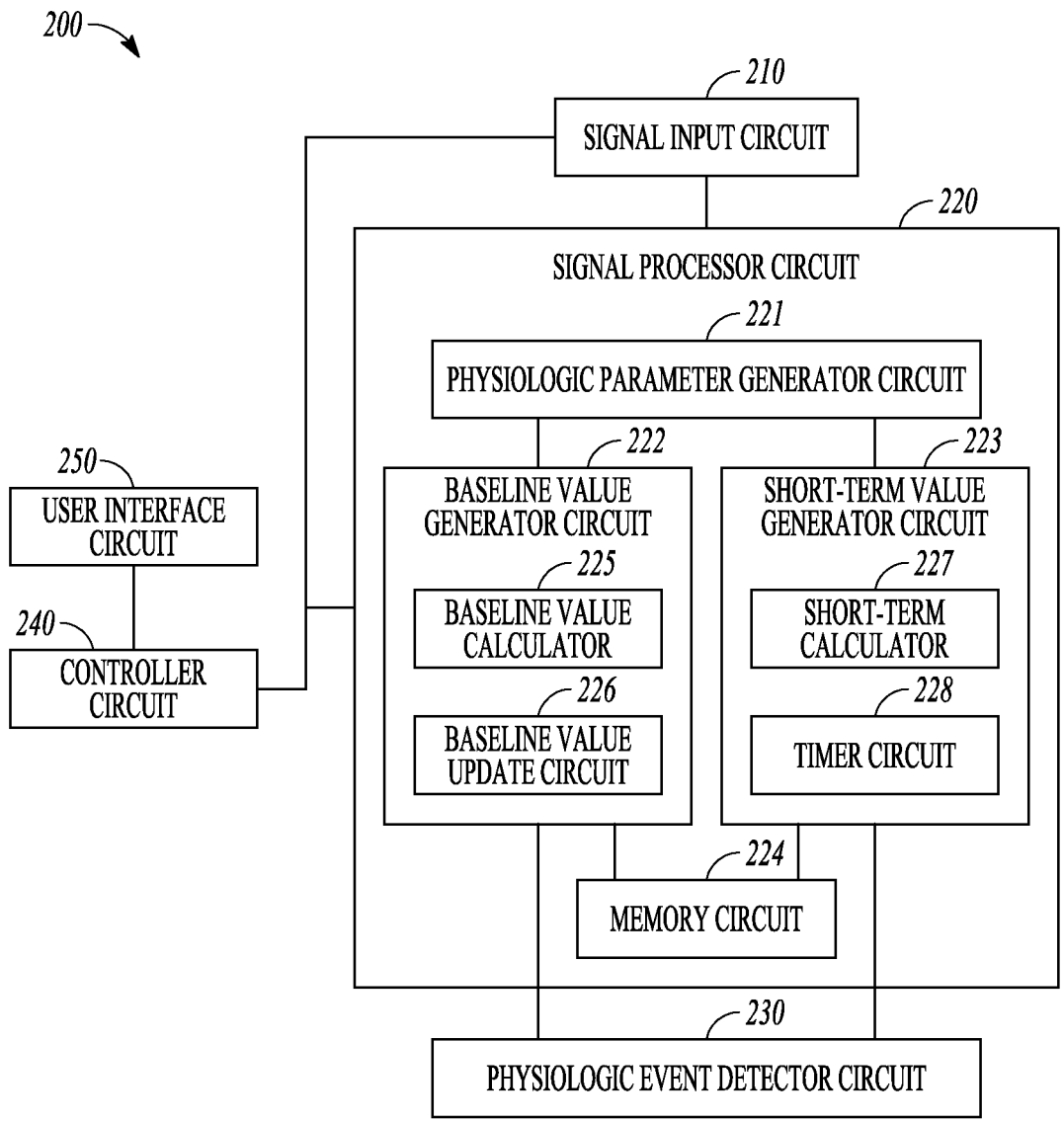
FIG. 2 illustrates generally an example of a target physiologic event detector.

FIG. 2 illustrates generally an example of a target physiologic event detector 200 that can be configured to detect a target physiologic event from a patient, such as a HF decompensation event or other worsening HF events. The target physiologic event detector 200 can be an embodiment of the worsening cardiac condition detector 113, and configured to detect worsening HF using at least one physiological signal sensed from the patient. The target physiologic event detector 200 can include one or more of a signal input circuit 210, a physiological signal processor circuit 220, a physiologic event detector circuit 230, a controller circuit 240, and a user interface unit 250.

The signal input circuit 210 can include a sense amplifier circuit to sense a physiological signal sensed from a patient, such as a physiological signal containing information indicative of status or progression of heart failure (HF). In an example, the sense amplifier circuit can be coupled to one or more electrodes such as the electrodes on one or more of the leads 108A-C or the can housing 112, one or more sensors, or one or more patient monitors, where the sensing circuit can sense at least one physiological signal from the patient. The signal input circuit 210 can include one or more other sub-circuits to digitize, filter, or perform other signal conditioning operations on the received physiological signal. In another example, the signal input circuit 210 can receive the one or more physiological signals from a storage device such as an electronic medical record (EMR) system, such as in response to a command signal provided by a system user, such as a clinician.

In an example, the signal input circuit 210 can be coupled to one or more electrodes on one or more of the leads 108A-C or the can housing 112 to measure a bioimpedance (Z) signal from a patient. The bioimpedance can include a plurality of measurements of thoracic impedance or cardiac impedance. The bioimpedance can be produced by injecting current between a first pair of electrodes and sensing the resultant voltage across a second pair of electrodes. For example, the bioimpedance can be sensed across an RA electrode 141 or 142 and the can housing 112 ($Z_{RA\text{-}Can}$), across an RV electrode 152, 153 or 154 and a can housing 112 ($Z_{RV\text{-}Can}$), or across an LV electrode selected from electrodes 161-164 and the can housing 112 ($Z_{RV\text{-}Can}$). The bioimpedance can include an impedance vector where the voltage sensing electrodes are the currently injection electrodes are orthogonal to each other, such as selected from RA, RV, or LV electrodes ($Z_{RA\text{-}RV\text{-}LV}$).

The signal input circuit 210 can alternatively or additionally receive one or more of electrocardiograph (ECG) or electrograms (EGM) such as sensed from electrodes on one or more of the leads 108A-C or the can housing 112, a pulmonary artery pressure signal, an RV pressure signal, an LV coronary pressure signal, a coronary blood temperature signal, a blood oxygen saturation signal, a heart sound (HS) signal that includes one or more of S1, S2, S3, or S4 hear sound components, or a respiration signal rate signal or a tidal volume signal, among others.

The physiological signal processor circuit 220, coupled to the signal input circuit 210, can generate characteristic values from the received signal for use in detection of a target HF event. In an example, the physiological signal processor circuit 220 can be implemented as a part of a microprocessor circuit. The microprocessor circuit can be a dedicated processor such as a digital signal processor, application specific integrated circuit (ASIC), microprocessor, or other type of processor for processing information including the physiological signals received from the signal input circuit 210. Alternatively, the microprocessor circuit can be a general purpose processor that can receive and execute a set of instructions of performing the functions, methods, or techniques described herein.

In an example such as illustrated in FIG. 2, the physiological signal processor circuit 220 can include circuit sets comprising one or more other circuits or sub-circuits, that may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the physiological signal processor circuit 220 can include a circuit set including a physiologic parameter generator circuit 221, a baseline value generator circuit 222, a short-term value generator circuit 223, and a memory circuit 224.

The physiologic parameter generator circuit 221 can extract from the sensed physiological signal one or more statistical or morphological parameters. Examples of the statistical parameters can include signal mean, median, or other central tendency measures, a histogram of the signal intensity, or one or more signal trends over time. Examples of the morphological parameters can include maximum or minimum within a specified time period such as a cardiac cycle, positive or negative slope or higher order statistics, signal power spectral density at a specified frequency range, among other morphological descriptors. In an example, the physiologic parameter generator circuit 221 can generate a composite signal parameter set such as using the two or more physiological signals.

In an example, the signal input circuit 210 can receive a thoracic or cardiac impedance signal according to a specified impedance sensing configuration, and the physiologic parameter generator circuit 221 can generate impedance parameters using specified portions of the received impedance signal, such as during specified time or during the occurrence of specified physiologic events. For example, the physiologic parameter generator circuit 221 can generate the impedance parameters using portions of the received impedance signal during identical phases of a cardiac cycle (such as within a certain time window relative to R-wave), or at identical phases of a respiratory cycle (such as within the inspiration phase, or the expiration phase). This may minimize or attenuate the interferences such as due to cardiac or respiratory activities, in the impedance measurements.

The physiologic parameter generator circuit 221 can generate a trend of physiologic parameters using impedance measurements collected during one or more impedance acquisition and analysis sessions. In an example, an impedance acquisition and analysis session can start between approximately 5 a.m. and 9 a.m. in the morning, and lasts for approximately 2-8 hours. In another example, the impedance acquisition and analysis session can be programmed to exclude certain time periods, such as night time, or when the patient is asleep. The impedance parameter can be determined as a median of multiple impedance measurements acquired during the impedance acquisition and analysis session. The resultant multiple impedance parameter values can be used by the baseline value generator circuit 222 and the short-term value generator circuit 223 to generate respective characteristic impedance values. In some examples, the physiologic parameter generator circuit 221 can sense two or more physiological signals such as according to two or more impedance sensing vectors, and can generate a composite impedance parameter using the two or more physiological signals.

The baseline value generator circuit 222 can include a baseline value calculator 225, and a baseline value update circuit 226. The baseline value calculator 225 can be coupled to the signal input circuit 210, and generate one or more baseline values using respective one or more first signal portions of the physiological signal during respective one or more first time durations. In an example, each of the baseline values can be a statistical measure of a set of impedance parameter values calculated during a corresponding first time window ($W_L$) having a first time duration, and the baseline value, which represents an impedance baseline ($Z_{BL}$), can be computed as a statistical measure among the first set of impedance parameter values during the first time window $W_L$. The statistical measure can include a mean, a median, a mode, a percentile, a quartile, or other statistical measures. In an example, the first time window $W_L$ can be between 1-6 months.

In an example, the baseline value generator circuit 222 can generate an initial baseline value using a first signal portion, and the baseline value update circuit 226 can generate the one or more baseline values by updating the initial baseline value using one or more third signal portions of the received physiological signal. The one or more third signal portions can postdate the first signal portion in time. In an example, the baseline value update circuit 226 can periodically, or upon receiving a command from a system user, update $Z_{BL}$ using a linear combination of historically computed $Z_{BL}$ and the impedance parameter values obtained from the more recent one or more third portions of the impedance signal. The baseline value generator circuit 222 can be coupled to a memory circuit 224 to store the baseline values in the memory circuit 224.

The short-term value generator circuit 223 can include a short-term value calculator 227 and a timer circuit 228. The short-term value calculator 227 can use respective one or more second portions of the physiological signal to generate one or more short-term values. In an example, the one or more short-term values can be statistical measures of one or more second sets of physiologic parameter values during respective second time windows $\{W\}=\{W_1, Ws_2, \ldots, W_N\}$ each having a specified time duration, where N is the number of second time windows. Examples of the statistical measures can include a mean, a median, a mode, a percentile, a quartile, or other measures of central tendency measures. In an example, at least some of the second time windows $\{W\}$ have shorter time duration than the corresponding first time windows. In some examples, at least a portion of the first time windows precedes the corresponding second time windows $\{W\}$ in time.

In an example where the received physiological signal includes thoracic or cardiac impedance signal, the short-term values can include characteristic short-term impedance values $\{Z\}=\{Z_1, Z_2, \ldots, Z_N\}$, where each $Z_i$ can be computed as a mean, a median, or other central tendency measure of a set of impedance parameter values during the respective second time window $W_i$. In an example, each of the second windows $\{W\}$ can be 24 hours in duration. In another example, each of the second windows $\{W\}$ can each be approximately 2-10 days, or 14-28 days. In another example where the received physiological signal includes heart sounds (HS) signal, the physiologic parameter extracted from the HS signal for use to detected target HF event can include intensity of a HS component, such as S3 intensity $\|S3\|$. The short-term values can include characteristic short-term $\|S3\|$ values $\{\|S3\|\}=\{\|S3\|_1, \|S3\|_2, \ldots \|S3\|_N\}$ determined during the second time windows $\{W\}=\{W_1, W_2, \ldots, W_N\}$, where each $\|S3\|_i$ can be computed as a mean, a median, or other central tendency measure of a set of $\|S3\|$ values during the respective second time window $W_i$.

The timer circuit 228 can be configured to produce timing information associated with respective one or more short-term values. The timings, denoted by $\{T\}=\{T_1, T_2, \ldots, T_N\}$, can represent temporal locations of each of the second time windows $\{W\}$. In an example, the timings $\{T\}$ can be determined as respective time intervals between $\{W\}$ and a reference time $T_{Ref}$, such as the time instant for detecting an impending HF event.

The memory circuit 224 can be coupled to the baseline value generator circuit 222 and the short-term value generator circuit 223, and store the baseline values and the short-term values. The timing information associated with the short-term values can also be stored in the memory circuit 224.

The physiologic event detector circuit 230 can be configured to detect a target physiologic event or condition, such as a physiologic event indicative of an onset of a disease, worsening of a disease state, or a change of a disease state. In an example, the physiologic event detector circuit 230 can detect the presence of an event indicative of HF decompensation status, worsening HF, pulmonary edema, pneumonia, or myocardial infarction, among others. In some examples, the physiologic event detector circuit 230 can generate a detection index (DI) using the one or more baseline values generated by the baseline value generator circuit 222, the one or more short-term values generated by the short-term value generator circuit 223, and the timing information associated with the one or more short-term values. In an example, the physiologic event detector circuit 230 can compute the DI using a combination of the difference values between the one or more short-term values and corresponding one or more baseline values, where the difference values can be scaled by respective weight factors determined using the timings of the one or more first signal portions or the one or more second signal portions. The DI can represent the trend of the physiologic parameter, such as the impedance parameter values, over time, and can indicate presence or severity of a physiologic condition precipitating a HF decompensation event, such as excessive thoracic fluid accumulation. Examples of computing the DI and using DI to detect a cardiac condition are discussed below, such as with reference to FIG. 3.

The controller circuit 240 can control the operations of the signal input circuit 210, the physiological signal processor circuit 220, the physiologic event detector circuit 230, and the data and instruction flow between these components. In an example, the controller circuit 240 can control the settings of electrical impedance sensing including, for example, selecting electrodes used for current injection and the electrodes used for sensing the resultant voltage, or a beginning and an end of an impedance acquisition and analysis session. In another example, the controller circuit 240 can initiate an impedance acquisition and analysis session in response to a detection of a triggering event such as a change of a physiologic state or a change of the patient's health condition, or a specific time of a day such as in the morning between 6 a.m. and 12 noon. Alternatively, the controller circuit 240 can use an indication of a sleep-to-awake state transition to initiate an impedance acquisition and analysis session for acquiring impedance measurement during specified time following the transition to the awake state.

The user interface unit 250 can be configured to present programming options to the user and receive user's programming input. The user interface unit 250 can include an input device, such as a keyboard, on-screen keyboard, mouse, trackball, touchpad, touch-screen, or other pointing or navigating devices. The input device can enable a system user to program the parameters used for sensing the physiological signals. The user interface can include an output unit that can generate a presentation of information including the detected cardiac condition. The information can be presented in a table, a chart, a diagram, or any other types of textual, tabular, or graphical presentation formats, for displaying to a system user. The presentation of the output information can include audio or other human-perceptible media format to alert the system user of the detected progression of cardiac condition. In an example, at least a portion of the user interface unit 250, such as the user interface, can be implemented in the external system 120.

In some examples, the target physiologic event detector 200 can additionally include a therapy circuit configured to deliver a therapy to the patient in response to the cardiac condition indicator. Examples of the therapy can include electrostimulation therapy delivered to the heart, a nerve tissue, or other target tissues in response to the detection of the target physiologic event.

Figure 3:
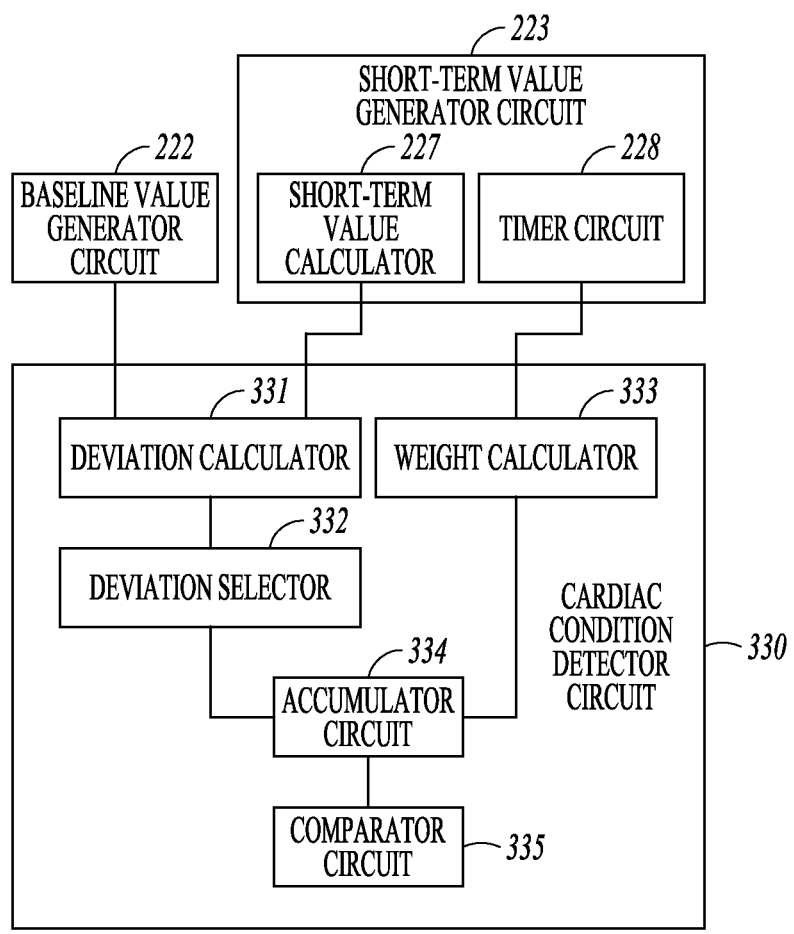
FIG. 3 illustrates generally an example of a heart failure (HF) event detector circuit.

FIG. 3 illustrates generally an example of a cardiac condition detector 330, which can be an example of the HF event detector circuit 230 of the target physiologic event detector 200 in FIG. The cardiac condition detector 330 can include one or more of a deviation calculator 331, a deviation selector 332, a weight calculator 333, an accumulator circuit 334, and a comparator circuit 335.

The deviation calculator 331 can be coupled to the baseline value generator circuit 222 and the short-term value calculator 227, and configured to compute relative deviations of the one or more short-term values, such as provided by the short-term value calculator 227, from the corresponding one or more baseline values such as provided by the baseline value generator circuit 222. Examples of the relative deviations can include a difference, a percentile change, or other relative difference measures. In an example where the received physiological signal includes thoracic or cardiac impedance signal, the deviation calculator 331 can compute the relative deviations including impedance difference $\{\Delta Z\}=\{\Delta Z_1, \Delta Z_2, \ldots, \Delta Z_N\}$ between the short-term impedance values $\{Z\}$ computed during the second time windows $\{W\}$ and the corresponding baseline impedance values $\{Z_{BL}\}$ computed using the baseline impedance during the first time windows, that is, $\Delta Z_i=Z_i-Z_{BLi}$ for $i=1, 2, \ldots, N$. Alternatively, the relative deviations can be represented as a percentile change with respect to the corresponding baseline impedance $Z_{BLi}$, that is, $\Delta Z_i\%=(Z_i-Z_{BLi})/Z_{BLi}$, for $i=1, 2, \ldots, N$. The relative difference can also be computed as a rate of change from $Z_i$ to $Z_{BLi}$, that is, $\Delta Z_i/\Delta t=(Z_{Si}-Z_{BLi})/(T_i-T_{BLi})$, where $T_{BLi}$ and $T_i$ are the time associated with the first and the second time window, respectively.

In another example where the received physiological signal includes heart sounds (HS) signal, the deviation calculator 331 can compute the S3 intensity deviations, $\{\Delta\|S3\|\}=\{\Delta\|S3\|_1, \Delta\|S3\|_2, \ldots, \Delta\|S3\|_N\}$, between the short-term $\|S3\|$ values $\{\|S3\|\}$ computed during the second time windows $\{W\}$ and the corresponding baseline impedance $\{\|S3\|BL\}$ computed using the baseline $\|S3\|$ during the first time windows, that is, $\Delta\|S3\|\mu_j=\|S^3\|_j-\|S3\|_{BLj}$, or percentile change $\Delta\|S3\|_j\%=(\|S3\|_j-\|S^3\|_{BLj})/\|S3\|_{BLj}$, or a rate of change from $\Delta\|S3\|_j/\Delta t=\|S3\|_{BL})/T_j-T_{BLj})$, where $T_{BL}$ and $T_j$ are the representative time for the first and the second time window, respectively.

The deviation selector 332 can be configured to select from the multiple relative deviations, such as N impedance difference $\{\Delta Z\}$ or M S3 heart sound intensity difference $\{\Delta\|S3\|\}$, a subset of the deviations that meet a specified criterion. In one example, the deviation selector 332 can select those $\Delta Z_i$ that satisfy $\Delta Z_i<0$. That is, only those $Z_i$ that are lower than $Z_{BL}$ are selected for use in detecting the target HF event. A reduction in impedance below the corresponding baseline level ($Z_{S_i}<Z_{BLi}$) can indicate increased buildup of thoracic fluid, which can be a precursor of decompensated HF. Using only the selected $\Delta Z_i$ indicative of HF decompensation can be more sensitive to an impending HF decompensation event. In another example, the deviation selector 332 can select those $\Delta\|S3\|_j$ that satisfy $\Delta\|S3\|_j>0$. That is, only those $\|S3\|_j$ that are greater than $\|S3\|_{BLj}$ are selected to detect the target HF event. An increase in S3 activity can indicate an elevated LV filing pressure, which may result in HF decompensated. For example, S3 amplitude can be related to filing pressures of the left ventricle during diastole, and correlated to left ventricular chamber stiffness and degree of restrictive filling. In another example, frequency of S3 can be related to ventricular stiffness and dimension. Therefore, an increase in $\|S3\|$ above a corresponding baseline level ($\|S3\|_j>\|S3\|_{BLj}$) can be an indication of elevated filing pressures and increased ventricular stiffness, an earlier precursor of decompensated HF. Using only those $\|S3\|_j$ indicative of HF decompensation can be more sensitive to an impending HF decompensation event.

The weight calculator 333 can generate one or more weight factors for at least some of the deviations such as generated by the deviation selector 332. In an example, the weight calculator 333 can be coupled to the timer circuit 228, and generate the weight factors $\{\omega\}=\{\omega_1, \omega_2, \ldots, \omega_N\}$ for the corresponding deviations $\{\Delta Z\}=\Delta Z_1, \Delta Z_2, \ldots, \Delta Z_N\}$ or $\{\Delta\|S3\|\}=\{\Delta\|S3\|_1, \Delta\|S3\|_2, \ldots, \Delta\|S3\|_N\}$, at least using the timing information associated with the one or more short-term values, such as the timings $\{T\}=\{T_1, T_2, \ldots, T_N\}$ of the second time windows $\{W\}$. Each weight factor $\omega_i$ can be a mathematical function of the corresponding timing $T_i$: $\omega_i=f(T_i)$. In an example, the function $f$ can be a decay function, such as an exponential decay function such that $\omega_i=A\cdot\exp(-kT_i)$, where A is a scale factor, and k is a positive number controlling the rate of decay of the weight factor $\omega_i$ as $T_i$ increases. The exponential decay function $f$ can alternatively be represented in a form of geometric progression, such that $\omega_i=A\cdot\lambda^i$ where A is a scale factor, and $\lambda$ is a common decay ratio having a value between 0 and 1. The weight factor sequence $\{\omega\}$ decays geometrically as the timing $T_i$ is farther away from the reference time $T_{Ref}$. In some examples, the function $f$ can be one of a logistic decay function, a logarithm decay function, or a linear or piecewise linear decay function. Examples of the decaying weight factors and scaling of the deviations such as $\{\Delta Z\}$ or $\{\Delta\|S3\|\}$ are discussed below, such as with reference to FIG. 4.

The accumulator 334 can compute a detection index (DI) using some or all of the deviations such as generated by the deviation selector 332. In an example, the DI can be an aggregation of the deviations scaled respectively by the weight factors such as generated by the weight calculator 333. The DI can be computed using a linear combination, such as a weighted sum, of the impedance deviations $\{\Delta Z\}$ or the $\|S3\|$ deviations, that is, $DI=\Sigma_{i=1}^N \omega_i\cdot\Delta Z_i$, or $DI=\Sigma_{i=1}^N \omega_i\cdot\Delta\|S3\|_i$. The DI can be a quantitative measure of aggregated deviation of a physiologic parameter from a baseline.

In an example, the accumulator 334 can compute the weighted sum of the deviations corresponding to the short-term windows $\{W\}$ that fall within a specified accumulation period, such as approximately 30 days preceding in time of the reference time $T_{Ref}$. The weighted sum of the deviations can be computed without using the deviation selector 332, such that all the deviations are accumulated at the accumulator 334 regardless of short-term value (e.g., $Z_i$ or $\|S3\|_j$) relative to the corresponding baseline value (e.g., $Z_{BLi}$ or $\|S3\|_{BLj}$). Such a method of computing DI is hereinafter referred to as "unconditional weighted accumulation" method.

In another example, the accumulator 334 can compute the DI using weighted sum of only a selected portion of the deviations that meet the specified selection criteria by the deviation selector 332. For example, only those impedance deviations $\Delta Z_i$, corresponding to the short-term windows $\{W\}$ within a specified accumulation period (such as 30 days prior to the reference time $T_{Ref}$), that satisfy $\Delta Z_i<0$, are selected for computing the DI. In another example, only those S3 intensity deviations $\Delta\|S3\|_i$, corresponding to the short-term windows $\{Ws\}$ falling within a specified accumulation period (such as 30 days prior to the reference time $T_{Ref}$), that satisfy $\Delta\|S3\|_i>0$, are selected for computing the DI.

In some examples, instead of accumulating all the deviations that satisfy $\Delta Z_i<0$ or $\Delta\|S3\|_i>0$ during the specified accumulation period, the accumulator 334 can accumulate the weighted deviations from the most recent near-term window $W_1$ (which is closest in time to $T_{Ref}$) up to the first near-term window $W_k$ where the corresponding deviation fails to satisfy the selection criteria, that is, $\Delta Z_k\geq 0$ or $\Delta\|S3\|_k\leq 0$. The accumulator 334 can then compute the DI as a weighted sum of the deviations corresponding to the near-term windows $W_1$ through $W_{k-1}$. Each of the selected deviations meets the selection criterion such as $\Delta Z_i<0$ or $\Delta\|S3\|_i>0$, for $i=1, 2, \ldots, k-1$. This method of computing DI is hereinafter referred to as "conditional weighted accumulation" method. The deviation selector 332 can then reset DI to zero upon reaching the near-term window $W_k$.

The comparator 335 can be configured to compare the DI, such as generated by the accumulator 334, to a specified condition, such as a threshold value or a specified range. The comparator 335 can generate an indication of detecting a HF event if the DI exceeds the threshold, or falls within the specified range. Examples of computing the DI using the weighted accumulation are discussed below, such as with reference to FIGS. 4-5.

Figure 4:
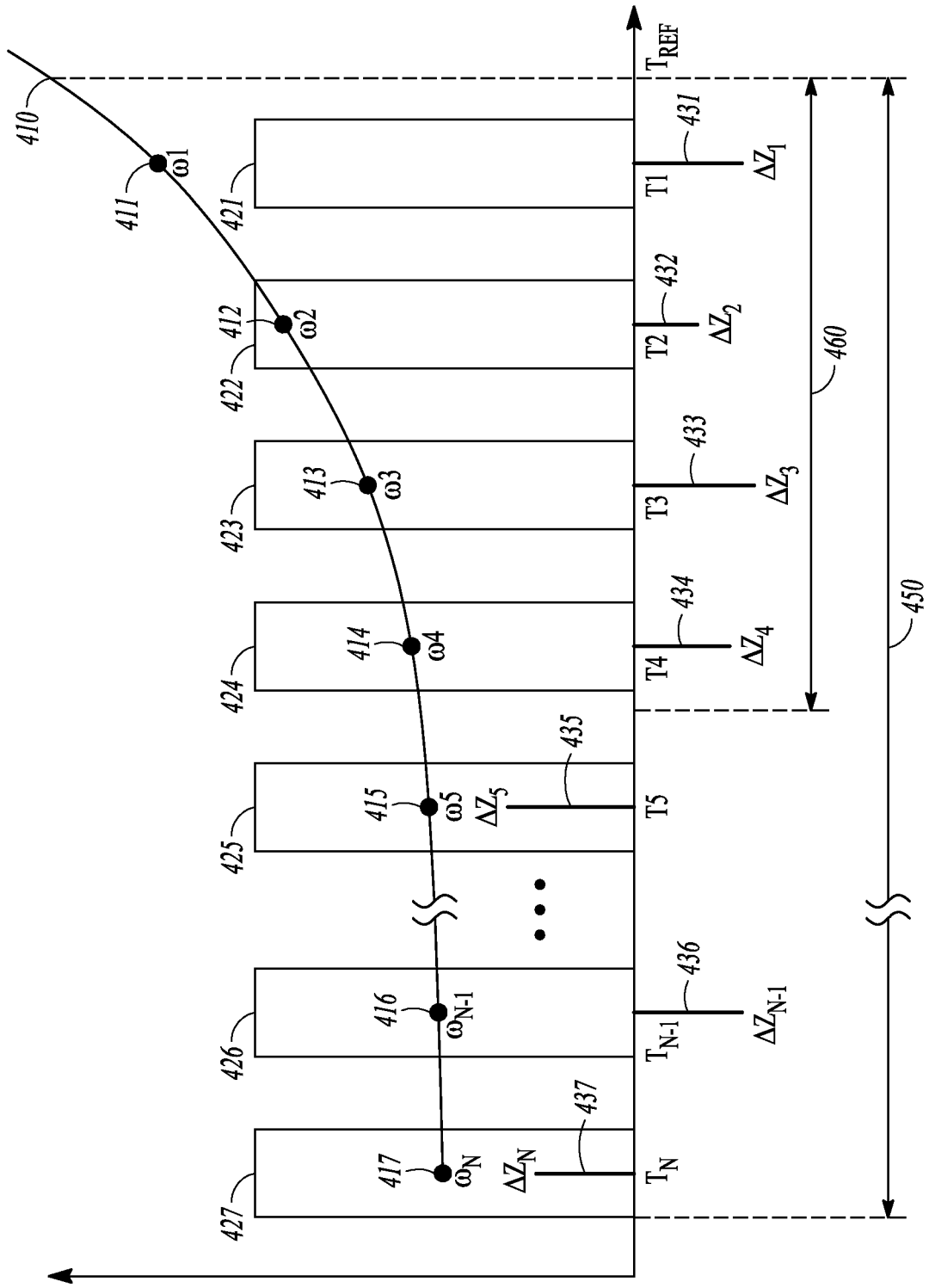
FIG. 4 illustrates generally an example of temporally weighted accumulation of the deviations using a decay function.

FIG. 4 illustrates generally an example of temporally weighted accumulation of the deviations using a decay function. The reference time ($T_{Ref}$) represents the time instant to make a decision of whether a target HF event, such as a HF decompensation event, is detected. A plurality of short-term values, such as characteristic short-term impedance values, can be computed as a mean, a median, or other central tendency or other statistical measure of the impedance values within the respective second time windows 421-427. Within the second time windows 421-427, impedance deviations $\Delta Z_1$ through $\Delta Z_N$ can be computed as, for example, difference or percentage difference values between the short-term impedance values and the corresponding baseline impedance values. As illustrated in FIG. 4, each impedance deviation $\Delta Z_i$ is associated with a timing $T_i$ that indicates a temporal location of the corresponding short-term window. For example, $T_i$ marks the timing of the first (most recent with respect to $T_{Ref}$) short-term window 421, and $T_N$ marks the timing of the last (most historical with respect to $T_{Ref}$) short-term window 427. In an example, the timings $T_1$ through $T_N$ can each be determined as the center of the respective short-term windows 421-427.

The weight factors 411-417, denoted by $\omega_1$ through $\omega_N$, correspond to the impedance deviations 431-437, denoted by $\Delta Z_1$ through $\Delta Z_N$, can be determined using the weight calculator 333 as shown in FIG. 3. A weight factor profile 410 describes the weight factors for the impedance deviations as a function of time. The weight factors $\omega_1$ through $\omega_N$ can each be calculated as a decay function of the timings $T_1$ through $T_N$. The decay function can be an exponential decay function, a logistic decay function, a logarithm decay function, or a linear or a piece-wise linear decay function. In an example, the weight factors $\omega_i$ can be determined as a decay function of a time interval between the respective timing $T_i$ and the reference time $T_{Ref}$, that is, $\omega_i = f(T_i - T_{Ref})$. In an example, the short-term windows $\{W\}$ can precede the reference time $T_{Ref}$ in time. As illustrated in FIG. 4, the decay function is an exponential function, and the weight factor $\omega_i$ can be computed as $\omega_i = A \cdot \exp[-k(T_{Ref} - T_i)]$. The deviations associated with the timings or the short-term windows farther away in time from the $T_{Ref}$ can therefore be weighted less than the deviations associated with the timings or the short-term windows closer in time to the $T_{Ref}$. For example, the weight factor for $\Delta Z_1$, $\omega_1 = A \cdot \exp[-k(T_{Ref} - T_1)]$, is greater than the weight factor for $\Delta Z_2$, $\omega_2 = A \cdot \exp[-k(T_{Ref} - T_2)]$.

A detection index (DI) can be computed using the accumulator circuit 334 as shown in FIG. 3. The DI can be computed using a combination of all, or a selected portion, of the weighted deviations. According to the "unconditional weighted accumulation" method as previously discussed, all the deviations within a specified accumulation period 450, such as 30 days, prior to $T_{Ref}$ which includes $\Delta Z_1$ through $\Delta Z_N$ as illustrated in FIG. 4, are used to compute the DI, that is, $DI = \sum_{i=1}^{N} \omega_i \cdot \Delta Z_i$. Alternatively, according to the "conditional weighted accumulation" method, only a portion of the impedance deviations that meet the selection criteria, such as $\Delta Z_i < 0$, can be used in the computation of DI. The accumulation period 460 can be from $T_{Ref}$ back to the first near-term window where the corresponding deviation fails to satisfy $\Delta Z_i < 0$. As illustrated in FIG. 4, $\Delta Z_1$ through $\Delta Z_4$ satisfy the condition $\Delta Z_i < 0$, and $\Delta Z_5$ is the first deviation that fails to satisfy $\Delta Z_i < 0$. Therefore, only $\Delta Z_1$ through $\Delta Z_4$ are used in computing DI, that is, $DI = \sum_{i=1}^{4} \omega_i \cdot \Delta Z_i$.

Figure 5:
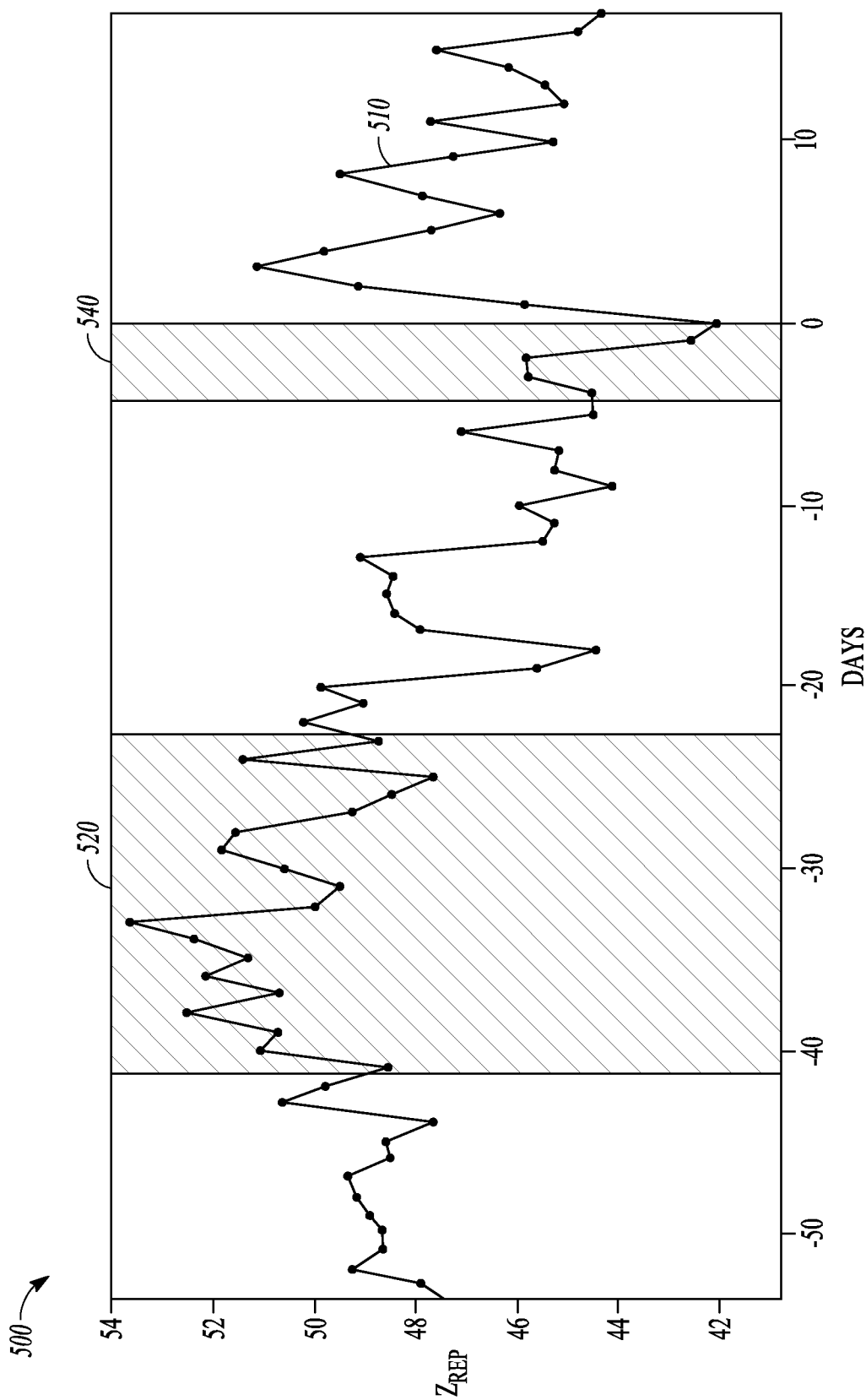
FIG. 5 illustrates generally an example of a portion of an impedance trend signal used for detecting a worsening HF event.

FIG. 5 illustrates generally an example of a trend 500 of impedance measurement (as shown in the y-axis) calculated over a period of approximately 70 days (as shown in the x-axis). The impedance measurements can be acquired by an impedance sensing circuit within an implantable medical device (IMD). The impedance sensing circuit can be configured to couple to one or more electrodes on the RV lead and the IMD housing and to acquire measurements from the RV-Can impedance vector ($Z_{RV-Can}$). Each impedance measurement, denoted by data points 510 in the trend 500, represents a characteristic impedance value (such as a median, a mean, or other statistical value) during a 24-hour impedance acquisition and analysis session. The representative impedance value can be generated such as by an impedance sensing circuit coupled to the signal input circuit 210.

A long-term window 520 and a short-term window 540 of the representative impedance values can be specified for use in detecting a target physiologic event, such as worsening of HF or an event indicative of HF decompensation. Statistical measures can be generated respectively using the impedance measurements in the long-term window 520 and the short-term window 540, and a detection decision can be made using a comparison between the statistical measures of the long-term window 520 and the statistical measures of the short-term window 540.

FIGS. 6A-D illustrate generally examples of trends of a detection index (DI) used for detecting a worsening HF event. One or more of an impedance trend 610, a difference impedance trend 620, a first DI trend 630, or a second DI trend 640 can be generated and presented to a system user such as via a display unit in the user interface unit 250.

Figure 6A:
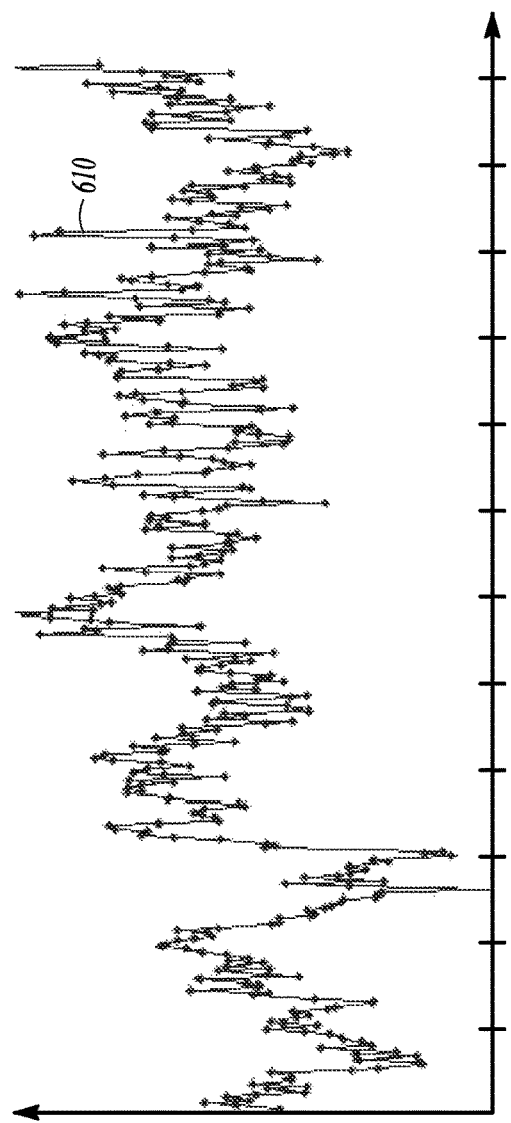
FIGS. 6A-D illustrate generally examples of trends of a detection index (DI).

FIG. 6A illustrates an impedance trend 610 that can include representative impedance values over a period of time. A portion of the trend 610 has a time span of approximately 12 months. Each data point in the trend 610 indicates a representative impedance value, which can be computed as a mean, a median, or other statistics of impedance measurements during a specified time period, such as a 24-hour impedance acquisition and analysis session. A baseline impedance value $Z_{BL}$ can be initialized to a mean, median, or other central tendency measure of impedance measurements within a long-term window having a duration of, for example, 30 days, and can be updated periodically using a linear combination of $Z_{BL}$ computed from an old window and the daily impedance value. Short-term impedance values $Z_S$ can be computed within short-term windows each having a duration of, for example, 24 hours.

Figure 6B:
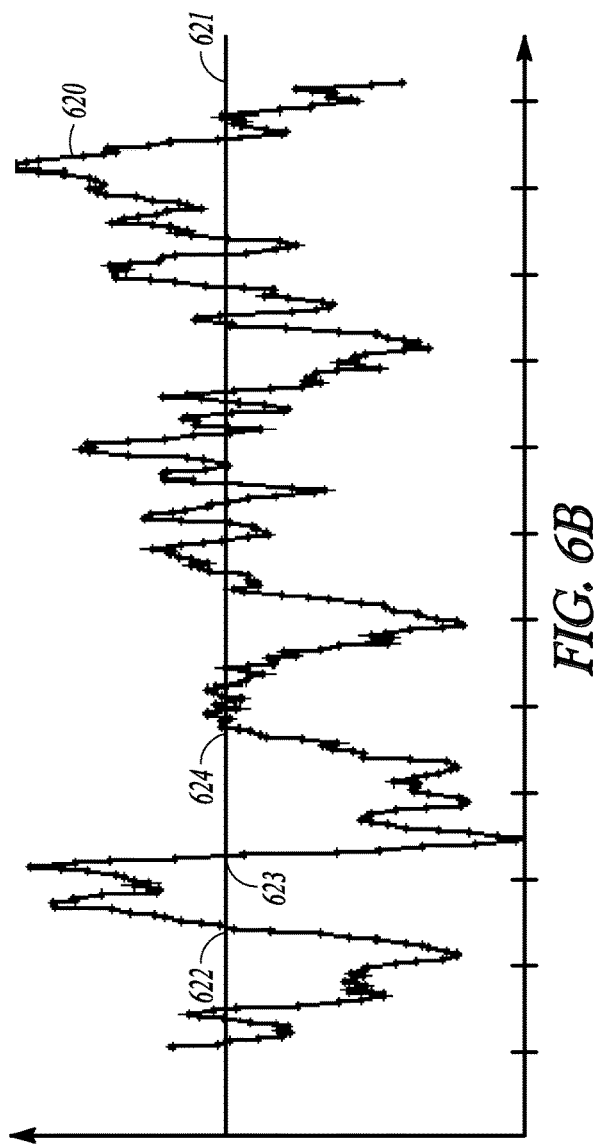

FIG. 6B illustrates a difference impedance trend 620 computed as the difference, $Z_{BL} - Z_S$, over time. The positive impedance difference that is above the zero line 621, such as a portion between zero-crossing points 622 and 623, indicates a period of sustained below-the-baseline thoracic impedance, i.e., negative deviations from the $Z_{BL}$ ($\Delta Z = Z_S - Z_{BL} < 0$). The below-the-baseline impedance may indicate increased thoracic fluid accumulation, a precursor of worsening HF or a HF decompensation event. The negative impedance difference that is below the zero line 621, such as a portion between the zero-crossing points 623 and 624, demonstrates a period of sustained above-the-baseline thoracic impedance, i.e., positive deviations from the $Z_{BL}$ ($\Delta Z = Z_S - Z_{BL} > 0$). Such an increase in thoracic impedance can be caused by reduced thoracic fluid accumulation, which is less likely an indication of worsening HF or a HF decompensation.

Figure 6C:
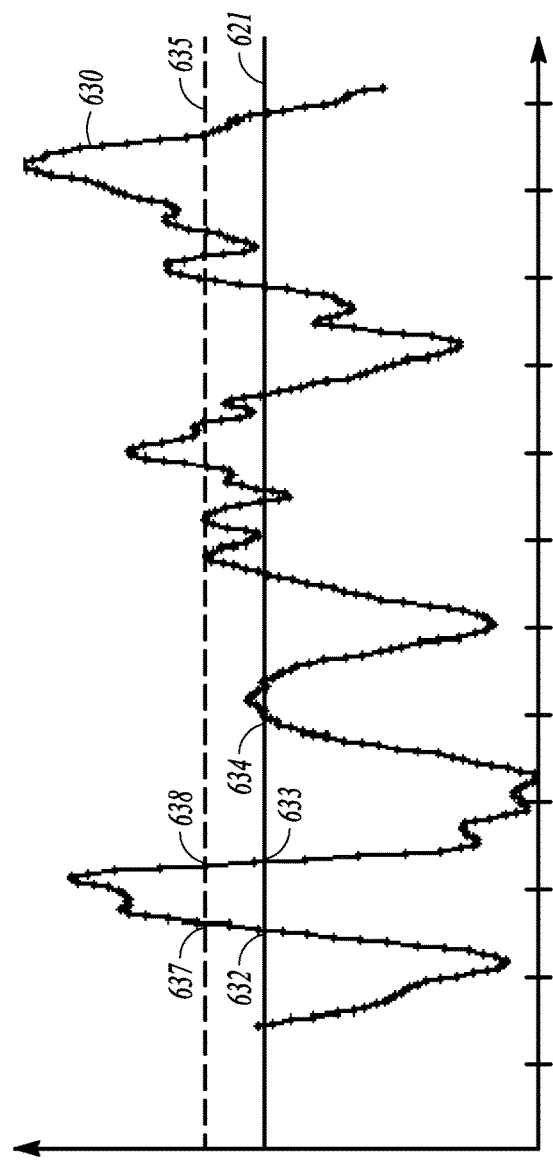

FIG. 6C illustrates a first DI trend 630 computed using the cardiac condition detector 330, in accordance with unconditional accumulation of 30-day deviations from the trend 620. The unconditional accumulation can have an effect of low-pass filtering of the trend 620, which may result in a smoother DI trend 630 compared to the trend 620. Positive portions of DI, such as between zero-crossing points 632 and 633, correspond to the positive portions of the trend 620 between the zero-crossing points 622 and 623; and negative portions of DI, such as between zero-crossing points 633 and 634, correspond to the negative portions of the trend between the zero-crossing points 623 and 624. The unconditional accumulation using the temporally decaying weight factors allows for preservation of local changes of impedance deviation in the DI trend 630. For example, the local sharp and quick changes in the trend 620 around the peaks between 622 and 623, or around the troughs between 623 and 624, are preserved in the DI trend 630, as can be seen in the corresponding portions around the peak DI between 632 and 633, or around the trough DI between 633 and 634. A DI threshold line 635 indicates the minimum level of DI used for detecting a worsening HF event. For example, a worsening HF event is deemed detected during the period when the DI trend 630 between threshold crossings 637 and 638 exceeds the threshold 635.

Figure 6D:
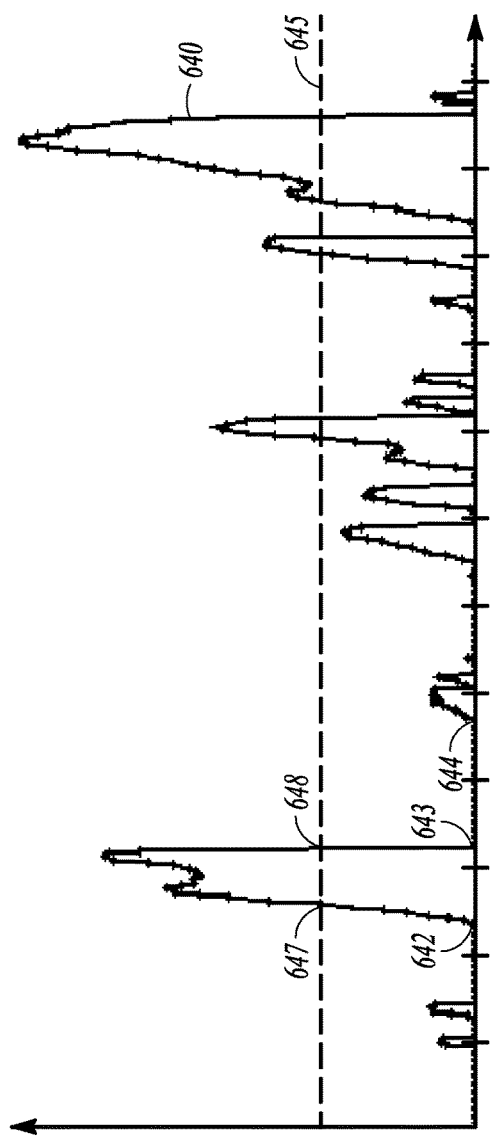

FIG. 6D illustrates a second DI trend 640 computed using the cardiac condition detector 330, in accordance with conditional accumulation of deviations from the trend 620. The conditional accumulation utilizes only the deviations, within a 30-day period prior to the reference time, that meet the condition of $\Delta Z<0$, or equivalently the positive impedance difference $Z_{BL}-Zs>0$ such as the portion of the trend 620 between zero-crossing points 622 and 623. The resultant accumulation, such as a portion between 642 and 643, corresponds to the positive portion of the trend 620 between the zero-crossing points 622 and 623. With respect to the negative portion of the trend 620 between the zero-crossing points 623 and 624 in which the impedance deviation $\Delta Z>0$, no accumulation is performed; and the DI can be reset to zero, as illustrated in the portion between 643 and 644. Similar to the DI trend 630, the conditional accumulation trend 640 also preserves of local changes around the peak impedance difference between 622 and 623, as demonstrated by the corresponding portions around the peak DI between 642 and 643. Similar to the threshold 635 for use with the DI trend 630, a threshold 645 can be used to detect a worsening HF event using the conditional accumulation trend 640, such as when the trend 640 between threshold crossings 647 and 648 exceeds the threshold 645.

Figure 7:
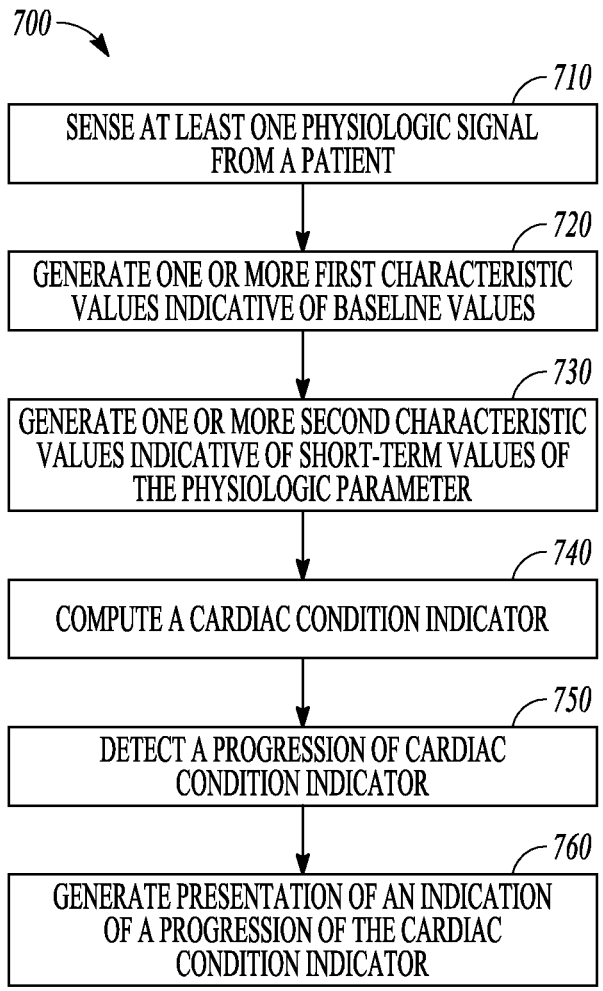
FIG. 7 illustrates generally an example of a method for detecting a target event indicative of progression of cardiac condition in a patient.

FIG. 7 illustrates generally an example of a method 700 for detecting a target event indicative of progression of cardiac condition in a patient. The target event can include a HF decompensation event, an event indicative of worsening HF, or an event indicative of recovery from a HF condition. The method 700 can be implemented and operate in an ambulatory medical device such as an implantable or wearable medical device, or in a remote patient management system. In an example, the method 700 can be performed by the worsening cardiac condition detector 113 or any embodiment thereof, or by the external system 120.

The method 700 begins at 710 by sensing at least one physiological signal from a patient. Examples of the physiological signal can include one or more of an electrocardiograph (ECG) or electrogram (EGM) such as sensed from electrodes on one or more of the leads 108A-C or the can housing 112, a bioimpedance signal, an arterial pressure signal, a pulmonary artery pressure signal, an RV pressure signal, an LV coronary pressure signal, a coronary blood temperature signal, a blood oxygen saturation signal, a heart sound (HS) signal, or a respiration signal rate signal or a tidal volume signal, among others. In an example, a thoracic or cardiac impedance signal can be sensed according a specified impedance vector that includes one or more electrodes on one or more of the implantable leads such as 108A-C or the can housing 112 implanted or otherwise attached to the patient. The impedance can be sensed in response to a detection of a triggering event such as a change of a physiologic state, a change of the patient's health condition, or a specific time of a day such as when the patient is awake.

The sensed impedance can be pre-processed, including one or more of signal amplification, digitization, filtering, or other signal conditioning operations. One or more statistical or morphological signal metrics can be extracted from the pre-processed signal.

At 720, one or more baseline values can be generated using one or more first signal portions of the sensed physiological signal. In an example where the received physiological signal includes thoracic or cardiac impedance signal, the baseline values can be baseline impedance values computed as a statistical measure (such as a mean or a median) of impedance values during respective time windows. In an example, the first time windows can be approximately 1-6 months. In some examples, the baseline values of the physiologic parameter can be generated by updating an initial baseline value, such as by using the baseline value update circuit 226 as illustrated in FIG. 2. For example, the baseline values of $Z_{BL}$ can be obtained using a linear combination of the initial baseline value and the impedance parameter values obtained from the more recent one or more third portions of the impedance signal.

At 730, one or more short-term values can be generated using respective one or more second signal portions of the received physiological signal. The one or more short-term values can each be statistical measures (such as a mean or a median) of one or more second sets of physiologic parameter values during respective second time windows $\{W\}=\{W_1, W_2, \ldots, W_N\}$. In an example, at least some of the second time windows $\{W\}$ can be shorter than the first window $W_L$. At least a portion of the first time window $W_L$ precedes each of the second time windows $\{W\}$ in time.

The short-term values can be associated with respective timings $\{T\}=\{T_1, T_2, \ldots, T_N\}$ that represent temporal locations of each of the second time windows $\{W\}$. In an example, the timings $\{T\}$ can be determined as respective time intervals between $\{W\}$ and a reference time $T_{Ref}$, such as the time instant for detecting an impending HF event.

At 740, a cardiac condition indicator can be generated using the one or more short-term values, the corresponding one or more baseline values, and the respective timings $\{T\}$ of the one or more second signal portions. In an example, the cardiac condition indicator is a detection index (DI) that can be computed using a linear or a non-linear combination of a difference, or a percentage difference or other relative difference, between the one or more short-term values and the corresponding one or more baseline values. Each difference can be scaled by a weight factor determined according to the timing information associated with the respective short-term value. Examples of generating the cardiac condition indicator are discussed below, such as with reference to FIGS. 8 and 9.

At 750, a progression of cardiac condition indicator, such as a worsening HF event or a HF decompensation event, can be detected. The cardiac condition indicator as calculated at 740 can be trended over time, and can periodically, or based on a command from a system user, be compared to a specified condition, such as a threshold value or a range of value. A target cardiac condition, such as worsening HF, is deemed detected if the cardiac condition indicator exceeds the threshold or falls within a specified range. At 760, information including the detection of the progression of cardiac condition indicator can be presented to the system user in a human-perceptible format in an output unit, such as a display or a user interface unit 250. In an example, the output information can be presented in a table, a chart, a diagram, or any other types of textual, tabular, or graphical presentation formats. In an example, an alert can be generated if a worsening HF is detected. The alert can be in audio or other human-perceptible media format. Additionally or alternatively, information such as a likelihood of a future heart failure decompensation event or a heart failure status can be determined using the cardiac condition indicator and displayed at 760. The method 700 can include a step of delivering a therapy, such as electrostimulation therapy delivered to the heart, a nerve tissue, or other target tissues in response to the detection of a worsening HF event.

Figure 8:
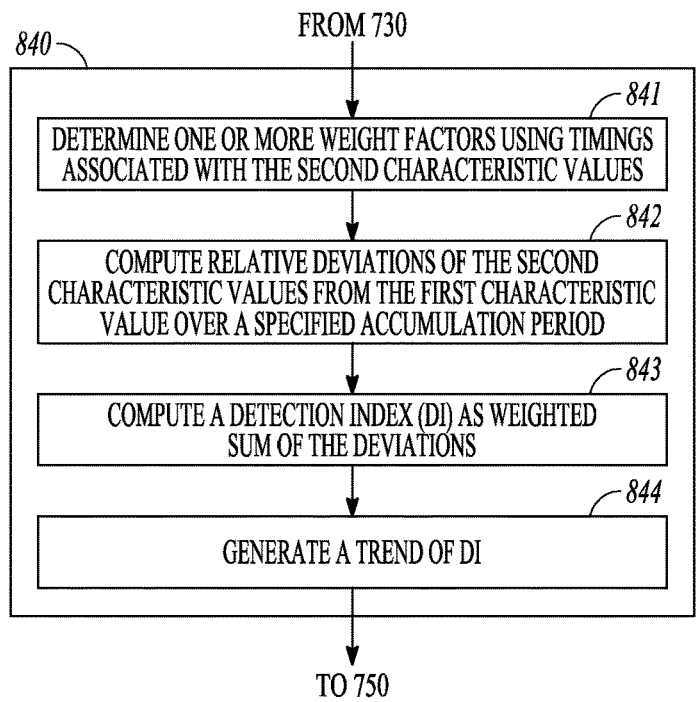
FIG. 8 illustrates generally an example of a method for computing a cardiac condition indicator.

FIG. 8 illustrates generally an example of a method 840 for computing a cardiac condition indicator. The method 840 can be an embodiment of the step 740 of the method 700. In an example, the method 840 can be implemented in and executed by the physiologic event detector circuit 230 as illustrated in FIG. 2, or the cardiac condition detector 330 as illustrated in FIG. 4.

The method 840, referred to as "unconditional weighted accumulation" method, begins at 841 by determining one or more weight factors for use in computing the cardiac condition indicator. The weight factors, $\{\omega\}=\{\omega_1, \omega_2, \ldots, \omega_N\}$, can be determined as a function $f$ of the corresponding timings $\{T\}=\{T_1, T_2, \ldots, T_N\}$ associated with the second time windows $\{W\}$ used for computing the one or more short-term values, that is, $\omega_i=f(T_i)$. In an example, the weight factors can be a decay function of time interval between the respective timing $T_i$ and the reference time $T_{Ref}$, that is, $\omega_i=f(Ti-T_{Ref})$. The reference time $T_{Ref}$ can be the time instant for detecting an impending HF event, and precedes the short-term windows $\{W\}$ in time. The weight factor $\omega_i$ decays such that a smaller weight can be associated with the deviation computed from more historical window $W_i$ (i.e., temporally more remote to $T_{Ref}$) than the deviation computed from more recent window $W_j$ (i.e., temporally closer to $T_{Ref}$). The function $f$ can be a decay function, such as at least one of an exponential decay function, a logistic decay function, a logarithm decay function, a linear decay function, or a piece-wise linear decay function. For example, the weight factor $\omega_i$ can be a exponentially decay function of $T_i-T_{Ref}$: $\omega_i=A\cdot\exp[-k(T_i-T_{Ref})]$, where A is a scale factor, and k is a positive number controlling the rate of decay of the weight factor $\omega_i$ as $T_i$ increases.

At 842, relative deviations of the short-term values from the corresponding one or more baseline values within a specified accumulation period can be computed. Examples of the relative deviations can include difference, percentile change, or other relative difference measures. In an example, the relative deviations can include impedance deviations $\{\Delta Z\}=\{\Delta Z_1, \Delta Z_2, \ldots, \Delta Z_N\}$ between the short-term impedance values $\{Z\}$ computed during the second time windows $\{W\}$ and the corresponding baseline impedance values $\{Z_{BL}\}$. In another example, the relative deviations can include a heart sound parameter, such as S3 heart sound intensity deviations, $\{\Delta\|S3\|\}=\{\Delta\|S3\|_1, \Delta\|S3\|_2, \ldots, \Delta\|S3\|_N\}$, between the short-term S3 intensity values $\{\|S3\|\}$ computed during the second time windows $\{W_S\}$ and the corresponding baseline $\|S3\|$ values $\{\|S3\|_{BL}\}$. In an example, the accumulation period can be 30 days.

At 843, a detection index (DI) can be computed using weighted sum of the deviations as generated at step 842, where each deviation can be scaled by the corresponding weight factor as generated at step 841. In an example, the DI can be computed using the impedance deviations $\{\Delta Z\}$: $DI=\Sigma_{i=1}^{N} \omega_i \cdot \Delta Z_i$. In another example, the DI can be computed using the S3 intensity deviations $\{\Delta\|S3\|\}$: $DI=\Sigma_{i=1}^{N} \omega_i \cdot \Delta\|S3\|_i$. The DI can be a quantitative measure of aggregated deviation of a physiologic parameter from a baseline. At 844, a DI trend can be generated such by continuously or periodically computing the DI at different time. The DI trend can then be used to detect a progression of cardiac condition indicator such as according to step 750 of the method 700.

Figure 9:
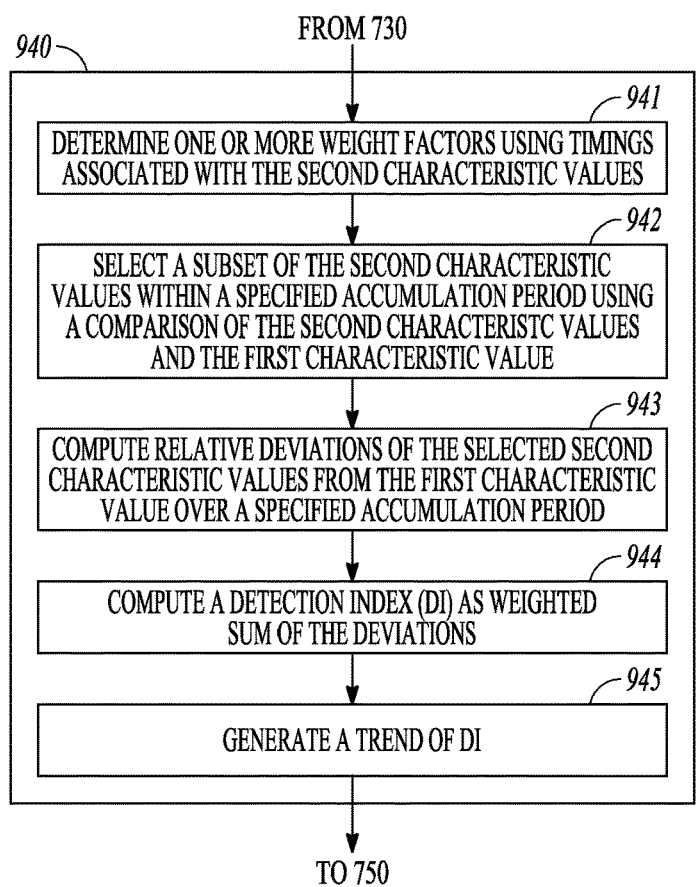
FIG. 9 illustrates generally another example of a method for computing a cardiac condition indicator.

FIG. 9 illustrates generally another example of a method 940 for computing a cardiac condition indicator. The method 940 can be an embodiment of the step 740 of the method 700. Similar to the method 840, the method 940 can be implemented in, and executed by, the physiologic event detector circuit 230 as illustrated in FIG. 2, or the cardiac condition detector 330 as illustrated in FIG. 4.

The method 940, referred to as "conditional weighted accumulation" method, begins at 941 by determining one or more weight factors for use in computing the cardiac condition indicator, which can be similar to the step 841 of the method 800. Then at 942, a subset of the short-term values within a specified accumulation period can be selected to compute the detection index (DI). In an example, the selected subset can include only those short-term impedance values $Z_i$ that are less than the corresponding baseline impedance value $Z_{BLi}$, that is, only those $Z_i$ that have negative deviations $\Delta Z_i<0$. In another example, the selected subset consists of only those short-term S3 intensity values $\|S3\|_j$ that are greater than the corresponding baseline S3 intensity $\|S3\|_{BLj}$, that is, only those $\|S3\|_j$ that have positive deviations $\Delta\|S3\|_j>0$. In an example, instead of accumulating all the deviations satisfying $\Delta Z_i<0$ or $\Delta\|S3\|_j>0$ during the specified accumulation period, only the deviations from the most recent near-term window $W_1$ (temporally closer to $T_{Ref}$) to the first near-term window $W_k$ where the corresponding deviation fails to satisfy the selection criteria (e.g., $\Delta Z_k\geq 0$ or $\Delta\|S3\|_k\leq 0$), are used in deviation accumulation.

At 943, relative deviations of the selected short-term values from the corresponding one or more baseline values over a specified accumulation period can be computed. Similar to the step 842 of method 800, the relative deviations can include difference, percentile change, or other relative difference measures. Then at 944, a detection index (DI) can be computed as weighted sum of the deviations as generated at step 943 using the corresponding weight factors as generated at step 941. For example, if the first K (K<N) impedance deviations $\{\Delta Z\}=\{\Delta Z_1, \Delta Z_2, \ldots, \Delta Z_K\}$, or the first K(K<N) S3 intensity deviations $\{\Delta\|S3\|\}_.=\{\Delta\|S3\|_1, \Delta\|S3\|_2, \ldots, \Delta\|S3\|_K\}$, are selected at 942, then the DI can be computed as $DI=\Sigma_{i=1}^{K} \omega_i \cdot \Delta Z_i$, or $DI=\Sigma_{i=1}^{K} \omega_i \cdot \Delta\|S3\|_i$. At 945, a DI trend can be generated such by continuously or periodically computing the DI. The DI trend can then be used to detect a progression of cardiac condition such as according to step 750 of the method 700.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with reference to the appended claims, along with the full scope of equivalents to which such claims are entitled.

What is claimed is:

1. A system, comprising:
a signal input circuit, including a sense amplifier circuit to receive at least one physiological signal sensed from a patient;
a memory circuit;
a baseline value generator circuit coupled to the signal input circuit and the memory circuit, the baseline value generator circuit configured to generate one or more baseline values using one or more first signal portions of the received at least one physiological signal during one or more first time durations, and to store the one or more baseline values in the memory circuit;
a short-term value generator circuit coupled to the signal input circuit and the memory circuit, the short-term value generator circuit configured to generate two or more short-term values using two or more second signal portions of the received at least one physiological signal during two or more second time durations, and to store the two or more short-term values in the memory circuit;
a comparator circuit coupled to the memory circuit or coupled to both the baseline value generator circuit and the short-term value generator circuit, the comparator circuit configured to determine differences between the two or more short-term values and the one or more baseline values; and
a cardiac condition detector circuit coupled to the comparator circuit, the cardiac condition detector circuit configured to detect a heart failure (HF) status using a weighted combination of the differences between the two or more short-term values and the one or more baseline values, wherein the weighting includes two or more weight factors determined using timings of when the two or more second signal portions are sensed from the patient,
wherein the weighted combination of the differences is computed regardless of whether the two or more short-term values are less than or greater than the one or more baseline values.

2. The system of claim 1, further comprising an output circuit coupled to the cardiac condition detector circuit, the output circuit configured to generate a human-perceptible presentation of the detected HF status.

3. The system of claim 1, wherein the cardiac condition detector circuit is configured to detect the HF status using a linear combination of the differences between the two or more short-term values and the one or more baseline values, the differences scaled by a respective weight factor.

4. The system of claim 1, wherein the two or more weight factors are determined as a decay function of time intervals between the timings of the two or more second signal portions and a reference time, the decay function including at least one of an exponential decay function, a logistic decay function, a logarithm decay function, a linear decay function, or a piece-wise linear decay function.

5. The system of claim 1, wherein the short-term value generator circuit is configured to generate the two or more short-term values using the two or more second signal portions that proceed a reference time.

6. The system of claim 1, further comprising a selector circuit coupled to the comparator circuit,
wherein the selector circuit is configured to select a subset of the two or more short-term values using the differences between the two or more short-term values and the one or more baseline values, and
wherein the cardiac condition detector circuit is configured to only use the selected subset of the two or more short-term values to detect the HF status.

7. The system of claim 1, wherein the at least one physiological signal sensed from the patient corresponds to an impedance signal, a thoracic impedance signal, a heart sound signal, an activity signal, a respiration signal, an S3 heart sound intensity signal, or a pressure signal.

8. The system of claim 1, wherein the cardiac condition detector circuit is configured to determine a likelihood of a future heart failure decompensation event, or to detect a worsening heart failure (WHF) event.

9. The system of claim 1, further comprising a therapy circuit configured to deliver a therapy to the patient in response to the detected HF status.

10. The system of claim 1, wherein the baseline value generator circuit is configured to generate a daily baseline value for a respective day using the one or more first signal portions of the received at least one physiologic signal for the respective day, wherein the short-term value generator circuit is configured to generate a daily short-term value for the respective day using one of the two or more second signal portions of the received at least one physiologic signal for the respective day, wherein the comparator circuit is configured to determine a daily difference for the respective day between the daily short-term value for the respective day and the daily baseline value for the respective day, and wherein the cardiac condition detector circuit is configured to detect the HF status using a weighted combination of determined daily differences for multiple respective days, each daily difference weighted using a timing of when the corresponding one of the two or more second signal portions is sensed from the patient for the determined daily difference.

11. The system of claim 10, wherein the weighting for the determined daily differences decreases as the timing of when the two or more second signal portions are sensed from the patient for the determined daily difference increases relative to a reference time at which the detection of HF status is initiated.

12. A method, comprising:
sensing at least one physiological signal from a patient using a physiologic sensor;
generating one or more baseline values using one or more first signal portions of the sensed at least one physiological signal during one or more first time durations;
generating two or more short-term values using two or more second signal portions of the sensed at least one physiological signal during two or more second time durations;
computing differences between the two or more short-term values and the one or more baseline values; and
detecting a heart failure (HF) status using a weighted combination of the differences between the two or more short-term values and the one or more baseline values, wherein the weighting includes two or more weight factors determined using timings of when the one or more first signal portions or the two or more second signal portions are sensed from the patient,
wherein the weighted combination of the differences is computed regardless of whether the two or more short-term values are less than or greater than the one or more baseline values.

13. The method of claim 12, further comprising generating a human-perceptible presentation of the detected HF status.

14. The method of claim 12, wherein the HF status is detected using a linear combination of the differences between the two or more short-term values and the one or more baseline values, the differences scaled by a respective weight factor.

15. The method of claim 12, wherein the two or more weight factors are determined as a decay function of time intervals between the timings of the two or more second signal portions and a reference time, the decay function including at least one of an exponential decay function, a logistic decay function, a logarithm decay function, a linear decay function, or a piece-wise linear decay function.

16. The method of claim 12, further comprising determining a likelihood of a future heart failure decompensation event, or detecting a worsening heart failure (WHF) event.

17. The method of claim 12, wherein generating one or more baseline values comprises generating a daily baseline value for a respective day using the one or more first signal portions of the received at least one physiologic signal for the respective day, wherein generating two or more short-term values comprises generating a daily short-term value for the respective day using one of the two or more second signal portions of the received at least one physiologic signal for the respective day, wherein computing the difference between the two or more short-term values and the one or more baseline values includes determining a daily difference for the respective day between the daily short-term value for the respective day and the daily baseline value for the respective day, and wherein detecting the HF status comprises using a weighted combination of determined daily differences for multiple respective days, each daily difference weighted using a timing of when the corresponding one of the two or more second signal portions is sensed from the patient for the determined daily difference.

18. A system, comprising:
a baseline value generator circuit configured to generate one or more baseline values using one or more first signal portions of a physiological signal during one or more first time durations;
a short-term value generator circuit configured to generate two or more short-term values using two or more second signal portions of the physiological signal during two or more second time durations;
a comparator circuit configured to determine differences between the two or more short-term values and the one or more baseline values; and
a cardiac condition detector circuit coupled to the comparator circuit, the cardiac condition detector circuit configured to detect a heart failure (HF) status using a weighted combination of the differences between the two or more short-term values and the one or more baseline values, wherein the weighting includes two or more weight factors determined using timings of when the one or more first signal portions or the two or more second signal portions are sensed from the patient,
wherein the weighted combination of the differences is computed regardless of whether the two or more short-term values are less than or greater than the one or more baseline values.

19. The system of claim 18, comprising a programmer or a remote patient monitor configured to be in communication with a data storage device configured to store the physiological signal.

20. The system of claim 18, wherein the baseline value generator circuit is configured to generate a daily baseline value for a respective day using the one or more first signal portions of the received at least one physiologic signal for the respective day, wherein the short-term value generator circuit is configured to generate a daily short-term value for the respective day using one of the two or more second signal portions of the received at least one physiologic signal for the respective day, wherein the comparator circuit is configured to determine a daily difference for the respective day between the daily short-term value for the respective day and the daily baseline value for the respective day, and wherein the cardiac condition detector circuit is configured to detect the HF status using a weighted combination of determined daily differences for multiple respective days, each daily difference weighted using a timing of when the corresponding one of the two or more second signal portions is sensed from the patient for the determined daily difference.

* * * * *